United States Patent
Sakamoto et al.

(10) Patent No.: US 6,888,026 B2
(45) Date of Patent: May 3, 2005

(54) METHOD FOR PRODUCING (METH) ACRYLIC ACID

(75) Inventors: Kazuhiko Sakamoto, Himeji (JP); Kazuo Ohkouchi, Himeji (JP); Tomohiro Nakae, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 32 days.

(21) Appl. No.: 10/254,863

(22) Filed: Sep. 26, 2002

(65) Prior Publication Data

US 2003/0065215 A1 Apr. 3, 2003

(30) Foreign Application Priority Data

Sep. 28, 2001 (JP) ........................................ 2001-304050

(51) Int. Cl.[7] ........................... C07C 51/42; C07C 57/02
(52) U.S. Cl. ..................... 562/600; 562/598; 562/531; 562/532; 562/538; 562/542
(58) Field of Search ............................. 562/512, 512.2, 562/523, 531, 532, 598, 600

(56) References Cited

U.S. PATENT DOCUMENTS

| 5,322,960 A | 6/1994 | Sakamoto et al. |
| 5,856,568 A | 1/1999 | Okamoto et al. |

FOREIGN PATENT DOCUMENTS

| EP | 0 085 898 | 8/1983 |
| EP | 1 041 062 | 10/2000 |
| JP | 62-120341 | * 6/1987 |
| JP | 6-345681 | 12/1994 |
| JP | 9-95465 | 4/1997 |

OTHER PUBLICATIONS

G. Laufenberg, "Selektivität und Stofftransport bei der Reversosmose organisch–wässriger Mehrkomponentensysteme", VDI Verlag, Düsseldorf XP 002228003, pp. 36–91, 1997.
Patent Abstracts of Japan, vol. 011, No. 317 (C–452) Oct. 15, 1987 & JP 62 106043 A (Mitsui Toatsu Chem. Inc.; Others: 02), May 16, 1987.

* cited by examiner

*Primary Examiner*—Johann R. Richter
*Assistant Examiner*—Karl Puttlitz
(74) *Attorney, Agent, or Firm*—Wenderoth, Lind & Ponack, L.L.P.

(57) ABSTRACT

An object of this invention is to provide a method for producing acrylic acid that enables to suppress adverse influence of byproducts during distillation and to accomplish long-term continuous operation of the acrylic acid production apparatus. This invention is directed to a method for producing (meth)acrylic acid comprising the step of isolating (meth)acrylic acid from a liquid containing (meth) acrylic acid by distillation wherein the liquid contains glyoxal (including its hydrate) in a concentration of 0.1 mass % or less.

6 Claims, 1 Drawing Sheet

METHOD FOR PRODUCING (METH) ACRYLIC ACID

BACKGROUND OF THE INVENTION

1. Field of the Invention

This invention relates to a method of suppressing polymerization of acrylic acid resulting from byproduct contained in an acrylic acid aqueous solution, and precipitation of such byproduct, and more particularly to a method for suppressing polymerization and precipitation in a distillation step of acrylic acid production process, in which part or all of a dischared liquid from the acrylic acid production process is recyled as a relfux, by recycling the discharged liquid as a reflux after permiating the discharged liquid through a reverse osmosis membrane.

2. Description of the Prior Art

Heretofore, a bulky amount of acrylic acid has been produced in a variety of large-scaled plants. A typical production process of acrylic acid comprises the step of reacting propylene and/or acrolein (hereinafter, abbreviated as "propylene") with a molecular oxygen-containing gas by catalytic gas-phase oxidation to yield reaction gas, the step of contacting the reaction gas with a collecting liquid such as water to yield an acrylic acid aqueous solution, and the step of obtaining crude acrylic acid by distillation of the acrylic acid aqueous solution for purification.

As a result of detailed analysis of the experiments conducted by the inventors of this application, they found that the reaction gas obtained by catalytic gas-phase oxidation of propylene contains, in addition to acrylic acid, unreacted acrolein, and byproducts such as formaldehyde, glyoxal, furfural, benzaldehyde, formic acid, acetic acid, and maleic acid. Consequently, the acrylic acid aqueous solution that has been obtained by contacting the reaction gas with the collecting liquid contains such byproducts mentioned above. It is required to eliminate impurities such as water and byproducts by distillation or its equivalent in order to obtain purified acrylic acid as a final product from the acrylic acid aqueous solution.

Since the relative volatility of acrylic acid to water or acetic acid is small, it is difficult to isolate acrylic acid by simply performing distillation. In view of this, there has been proposed various azeotropic distillation methods for isolating acrylic acid by adding an azeotropic solvent to an acrylic acid aqueous solution for distillation and by extracting a mixture of acetic acid, water, and the azeotropic solvent as distillate.

In such an azeotropic distillation, it is required to set the distillation temperature high in order to remove impurities such as acetic acid whose boiling point is relatively high. Setting the distillation temperature high may likely to cause polymerization of acrylic acid. In view of this, a variety of polymerization inhibitors are fed to the distillation step in order to carry out long-term stable distillation while preventing polymerization of acrylic acid in an attempt to securely prevent polymerization of acrylic acid.

Japanese Unexamined Patent Publication No. HEI 9-95465, for example, discloses a method for preventing polymerization of acrylic acid by introducing copper salt compounds along with N-nitrosophenylhydroxyamine or its salts to a distillation column. Japanese Unexamined Patent Publication No. HEI 6-345681 discloses a method for preventing polymerization of acrylic acid in a distillation column by using 3-component polymerization inhibitor containing N-oxyl compound, phenol compound, and phenothiazine compound in combination with molecular oxygen.

Despite proposal of the various methods, the conventional polymerization inhibitors do not provide sufficient effect in suppressing polymerization of acrylic acid resulting from such byproducts, and precipitation of such byproducts.

Recently, there has been proposed reuse of discharge liquid obtained from the distillation step of isolating acrylic acid, as a collecting liquid which is used to contact with the reaction gas obtained by catalytic gas-phase oxidation of propylene, etc. However, such a discharge liquid contains the aforementioned byproducts. In long-term operation, as the number of times of reusing such a discharge liquid increases, the concentration of the byproducts in the acrylic acid aqueous solution is raised. When acrylic acid is isolated from such an aqueous solution containing the byproducts in high concentration by distillation, it is highly likely that acrylic acid is polymerized due to the byproducts. Adding a polymerization inhibitor in such a high concentrated condition may not effectively suppress the polymerization. Further, such byproducts may be condensed to result in reaction products. Moreover, if such byproducts may polymerize to oligomers, they may likely to precipitate in the distillation column, which resultantly varies the distribution of liquid phase or gas phase in the distillation column and lowers distillation efficiency. Further, the polymerization inhibitor in the distillation column may be distributed unevenly, thus resulting in lowering polymerization suppressive effect or failing to accomplish long-term stable operation of the distillation column.

SUMMARY OF THE INVENTION

A method which has accomplished the above object, according to this invention, is directed to a method for producing (meth)acrylic acid comprising the step of isolating (meth)acrylic acid from a liquid containing (meth)acrylic acid by distillation wherein the liquid contains glyoxal (including its hydrate) in a concentration of 0.1 mass % or less.

According to another aspect of this invention, a method for producing (meth)acrylic acid in which a collecting liquid is contacted with a mixed gas obtainable by using propylene and/or acrolein, or a mixed gas obtainable by using at least one compound selected from the group consisting of isobutylene, t-butylalcohol, and methacrolein to obtain a (meth)acrylic acid aqueous solution, the collecting liquid is separated from a discharge liquid obtained from the step of isolating (meth)acrylic acid from the (meth)acrylic acid aqueous solution for recycling along a reflux line.

DETAILED DESCRIPTION OF THE PREFERRED EMBODIMENTS OF THE INVENTION

Figure 1:
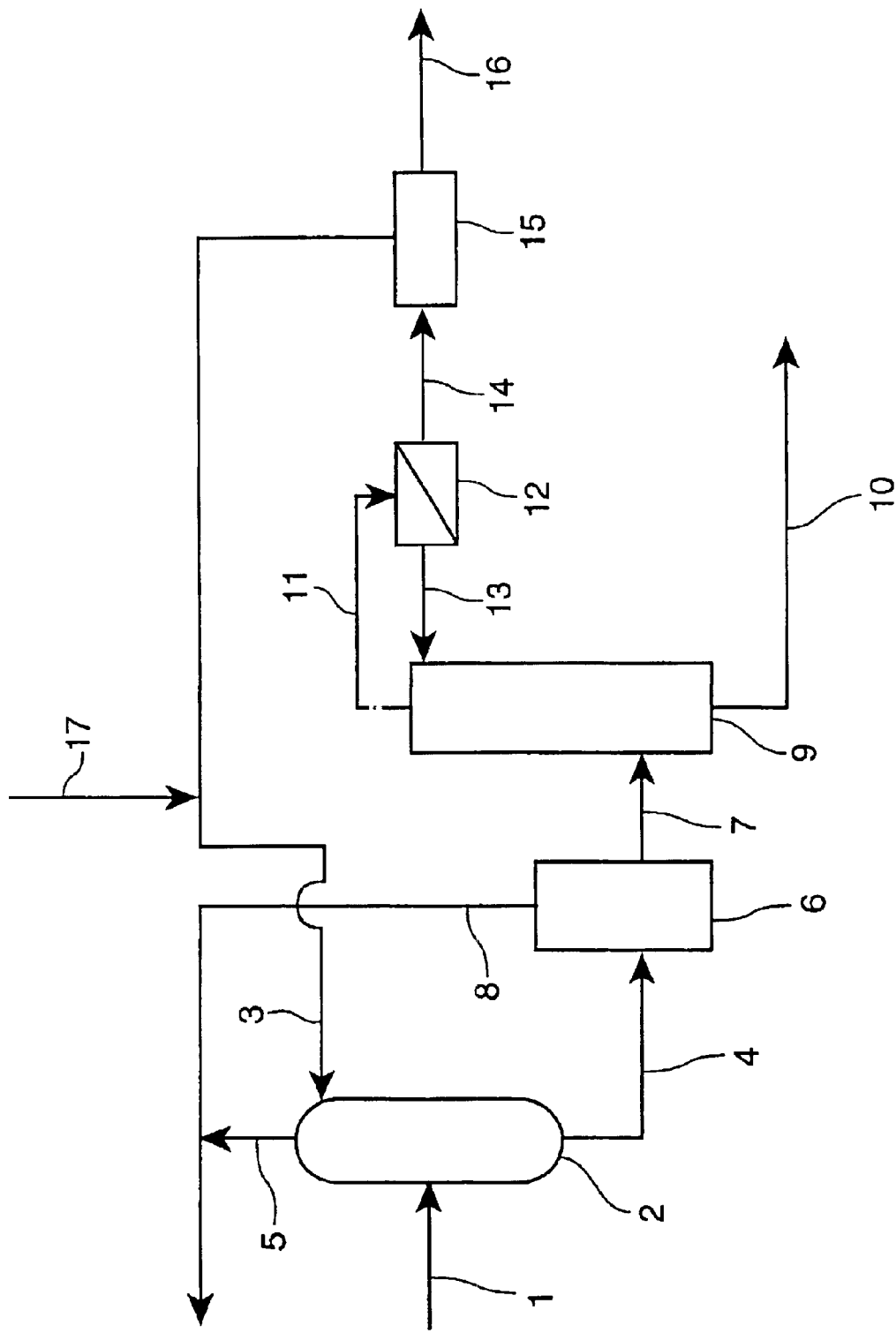
FIG. 1 is a schematic diagram illustrating an embodiment of an acrylic acid production method according to this invention.

In view of the above problems reside in the prior art, it is an object of this invention to provide a method for producing acrylic acid that enables to suppress adverse influence of byproducts during distillation and to accomplish long-term continuous operation of the acrylic acid production apparatus.

As mentioned above, this invention is directed to a method for producing (meth)acrylic acid comprising the step of isolating (meth)acrylic acid from a liquid containing (meth)acrylic acid by distillation wherein the liquid contains glyoxal (including its hydrate) in a concentration of 0.1 mass % or less. An exemplified liquid containing (meth)acrylic acid to which the inventive method is applied is preferably a (meth)acrylic acid aqueous solution, which is described later. According to another aspect of this invention, a method for producing (meth)acrylic acid in which a collecting liquid is contacted with a mixed gas obtainable by using propylene and/or acrolein, or a mixed gas obtainable by using at least one compound selected from the group consisting of isobutylene, t-butylalcohol, and methacrolein to obtain a (meth)acrylic acid aqueous solution, the collecting liquid is separated from a discharged liquid obtained in the step of isolating (meth)acrylic acid from the (meth)acrylic acid aqueous solution for recycling the collecting liquid along a reflux line. The method comprises the step of separating part or all of the collecting liquid circulating in the reflux line into an impermeated liquid and a permeated liquid by a reverse osmosis membrane to recycle all or part of the permeated liquid as the collecting liquid. permeating the discharged liquid with use of a reverse osmosis membrane enables to reduce the concentration of byproducts such as glyoxal in the permeated liquid. Using the permeated liquid as the collecting liquid enables to effectively suppress polymerization of acrylic acid resulting from the byproducts such as glyoxal, and precipitation of such byproducts.

Hereinafter, an exemplified inventive method is described by referring to an acrylic acid production process illustrated in FIG. 1. A primary feature of the inventive method resides in processing part or all of the collecting liquid circulating in the reflux line with use of a reverse osmosis membrane. The other steps of the production process are not specifically limited. The inventive method is not limited to the production process as stated below, and as far as not impairing the effects of this invention, any modification and alteration is applicable to the production process.

First, a mixed gas obtainable by using propylene and/or acrolein is fed from a line 1 to a collecting column 2. The mixed gas may be a reaction gas obtained by reacting propylene and/or acrolein with a molecular oxygen-containing gas or the like by catalytic gas-phase oxidation under an arbitrary condition. A collecting liquid, which is described later, is fed to the collecting column 2 via a line 3 to contact with the mixed gas (reaction gas) in the collecting column 2 to collect crude acrylic acid contained in the mixed gas. The collected crude acrylic acid is fed to a next step in the form of an acrylic acid aqueous solution via a line 4. Residue matters other than the crude acrylic acid generated in the collecting column 2 may be discharged outside of the collecting column 2 via a line 5. For example, these matters are recycled for the catalytic gas-phase oxidation, or fed to another step for combustion. According to this invention, the method/requirements for obtaining the mixed gas by catalytic gas-phase oxidation of propylene, and the method/requirements for obtaining a (meth)acrylic acid aqueous solution by contacting the mixed gas with the collecting liquid are not specifically limited to the one described in this embodiment.

As mentioned above, the acrylic acid aqueous solution contains byproducts such as formaldehyde, glyoxal, furfural, benzaldehyde, formic acid, acetic acid, and maleic acid and remainders such as acrolein which remain in a non-reactive state in addition to acrylic acid.

The acrylic acid aqueous solution may be directly fed to an azeotropic distillation column 9 via the line 4. Alternatively, an arbitrary step may be provided between the azeotropic distillation column 9 and the collecting column 2. For example, a stripping column 6 may be provided between the collecting column 2 and the azeotropic distillation column 9 to reduce the content of acrolein remaining in the acrylic acid aqueous solution. The aqueous solution after removal of acrolein in the stripping column 6 is fed to the azeotropic distillation column 9 via a line 7. In this embodiment, an azeotropic distillation column is used in which dehydrating distillation is carried out with use of an azeotropic solvent which forms azeotrope with water. Alternatively, it is possible to isolate (meth)acrylic acid from a (meth)acrylic acid aqueous solution by an arbitrary distillation unit in place of such an azeotropic distillation column. The way of distillation, requirements for distillation, number of distillations, arrangement of the distillation unit can be optionally selected according to the purpose of distillation.

According to this invention, as far as an azeotropic solvent has such a property that it forms azeotrope with water, any kind of azeotropic solvent is usable. It is desirable, however, to use an azeotropic solvent having such a property that it forms azeotrope with water and acetic acid, and yet does not form azeotrope with acrylic acid. An azeotropic solvent that is hardly soluble in water is recommended because it is easily separated from the discharge liquid (distillated water phase component) when recycling and reusing the solvent, which is described later. Some examples of such azeotropic solvent are toluene, xylene, hexane, heptane, cyclohexane, methylisobutylketone, and butyl acetate. The azeotropic solvent may be used alone or in combination according to the purpose of use. It is recommended to use aliphatic compounds of hydrocarbons having the number of carbon atoms from 7 to 8 such as heptane, and aromatic compounds of hydrocarbons having the number of carbon atoms from 7 to 8 such as toluene. Distillation with use of such an azeotropic solvent (aliphatic compounds of hydrocarbons having the number of carbon atoms from 7 to 8, or aromatic compounds of hydrocarbons having the number of carbon atoms from 7 to 8) easily separates the aqueous solution in the column 9 into two phases, i.e., oily phase and water phase. This arrangement facilitates condensation of byproducts in the water phase. The lower limit of the number of carbon atoms in the hydrocarbons is set at 7 for the following reason. If the number of carbon atoms is less than 7, the amount of water extracted by azeotropic distillation is reduced, which resultantly necessitates consumption of much calorie for azeotropic dehydration distillation. The upper limit of the number of carbon atoms in the hydrocarbons is set at 8 for the following reason. If the number of carbon atoms exceeds 8, the boiling point of the azeotropic solvent is raised, which makes it difficult to remove the azeotropic solvent along with water, and may likely to raise the content of the azeotropic solvent in the bottom liquid of the column 9.

The amount of the azeotropic solvent to be added to the column 9 is not limited. It is desirable, however, to use an appropriate amount of azeotropic solvent capable of obtaining sufficient acrylic acid separation effect to secure improved azeotropic distillation performance. According to this invention, as will be described later, a solvent separation tank 12 such as a decanter is used for separating the azeotropic solvent from the distillate discharged from a top part of the azeotropic distillation column 9 for reuse of the separated solvent. The solvent separated in the tank 12 is refluxed to an upper part of the column 9 via a line 13. In this instant, as far as the solvent evaporates with water in the azeotropic distillation column 9, the feeding position of the solvent is not limited. It is possible to feed an azeotropic solvent separately via an unillustrated line. As far as applicable to the inventive acrylic acid production process, the operating condition of the azeotropic distillation column 9 is not limited.

According to this invention, isolating (meth)acrylic acid from a (meth)acrylic acid aqueous solution includes, for example, carrying out an azeotropic distillation step in which an acrylic acid aqueous solution is fed to an azeotropic distillation column to separate and obtain acrylic acid substantially having been removed of acetic acid, water, and azeotropic solvent from the bottom of the column by a single distillation operation, as well as carrying out the steps of feeding an acrylic acid aqueous solution to an azeotropic distillation column for removal of water and azeotropic solvent, and feeding the bottom liquid (acrylic acid) in the azeotropic distillation column to an arbitrary unit such as an unillustrated acetic acid separation column for obtaining purified (meth)acrylic acid. In other words, according to this invention, the separation and purification steps of obtaining purified (meth)acrylic acid, which are applied to a known (meth)acrylic acid production process, can be optionally combined depending on the purpose of use of (meth)acrylic acid and the operating condition of the production apparatus.

In case of obtaining acrylic acid by one time distillation as shown in FIG. 1, preferably, the reflux ratio, the ratio of the liquid reflux to overhead product, in the azeotropic distillation column 9 ranges from 1.1 to 1.6, more preferably, 1.2 to 1.5, and furthermore preferably, 1.3 to 1.5. If the reflux ratio is less than 1.1, it is likely that the distillate of acrylic acid discharged from the top part of the column 9 may increase. If the reflux ratio exceeds 1.6, it is likely that the concentration of solvent in the bottom liquid may increase. Preferably, the temperature at the column top ranges from 45 to 55° C. If the temperature at the column top is less than 45° C., it is required to provide an additional cooling facility to cool distillated gas from the column top, which is not desirable in terms of cost. On the other hand, if the column top temperature exceeds 55° C., it is likely that the distillate of acrylic acid from the column top may increase. Also, preferably, the temperature at the bottom part of the column 9 ranges from 100 to 110° C . If the column bottom temperature exceeds 110° C., dimers of acrylic acid may increase in the bottom liquid, thus lowering the yield of purified acrylic acid. It is desirable to control the distillation conditions such that the concentration of acetic acid in the bottom liquid is 0.1 mass % or lower, preferably, 0.05 mass % or lower, and more preferably, 0.03 mass % or lower. Further, it is preferable to feed a polymerization inhibitor to the respective steps via unillustrated feeding means.

As far as exhibiting polymerization suppressive effect with respect to (meth)acrylic acid, the polymerization inhibitor is not specifically limited. Exemplified polymerization inhibitors are hydroquinone, methoquinone, phenothiazine, copper dibutyldithiocarbamate, manganese acetate, 4-hydroxy-2,2,6,6-tetramethylpiperidinoxyl, 1,4-dihydroxy-2,2,6,6-tetramethylpiperidine, 4-hydroxy-2,2,6,6-tetramethylpiperidine, and nitrosophenol. The polymerization inhibitor may be used alone or in combination, and the composition thereof may be optionally determined according to the purpose of use.

The amount of polymerization inhibitor may be optionally determined according to the operating condition of the azeotropic distillation column, and is not specifically limited. It is, however, desirable to set the total feeding amount of polymerization inhibitor to the evaporated vapor amount of acrylic acid in the range from 5 to 2000 ppm. In case that the total feeding amount of polymerization inhibitor is less than 5 ppm, polymerization in the azeotropic distillation column cannot be sufficiently suppressed. In case that the total feeding amount of polymerization inhibitor exceeds 2000 ppm, it is economically undesirable and there arises a problem such that acrylic acid as a final product may be colored. It should be appreciated that the evaporated vapor amount of acrylic acid is equivalent to the quantity of heat transferred to the azeotropic distillation column from heating means (not shown) such as a reboiler of the azeotropic distillation column, and corresponds to the total amount of vapors of monomers evaporated from the bottom liquid in the column.

The manner of feeding the polymerization inhibitor is not specifically limited. As an example, the polymerization inhibitor may be added in advance to a liquid such as an acrylic acid aqueous solution and a reflux liquid, and the mixture may be fed to the column 9. Alternatively, it is possible to directly feed the polymerization inhibitor (the polymerization inhibitor may be in any one of powdery, liquefied, and gaseous states) to the column 9. For example, in the case where molecular oxygen is fed to the column 9 as the polymerization inhibitor, the polymerization inhibitor may be directly fed through the bottom of the column 9 by an air bubbling or its equivalent. As an altered form, the polymerization inhibitor may be dissolved in a solvent for indirect feeding to the column 9. Particularly, it is recommended to feed molecular oxygen in a gaseous form through the bottom of the column 9 because installment of feeding means such as an air bubbling is easy. It is preferable to feed molecular oxygen of about 0.1 to 1.0 volumetric % to the total evaporation amount of acrylic acid to securely obtain desirable polymerization suppressive effect.

Referring back to the operation in the azeotropic distillation column 9, the acrylic acid aqueous solution fed to the column 9 is subjected to azeotropic distillation, and the low-boiling-components such as water and byproducts are discharged as a discharged liquid (hereinafter, sometimes referred to as "distillate") through the top part of the column 9 along with the azeotropic solvent. Acrylic acid in the aqueous solution is discharged through the bottom of the column 9 to a next step via a line 10.

According to this invention, the expression "separating the collecting liquid from the discharged liquid (distillated water phase component)" includes a case that the discharged liquid (distillated water phase component) is brought to an arbitrary step for use of part or all of the processed discharge liquid (distillated water phase component) as a collecting liquid, and a case that part or all of the discharged liquid (distillated water phase component) is used as a collecting liquid without subjecting the discharged liquid to another process.

According to this invention, mixture of the discharged liquid (distillated water phase component) and the azeotropic solvent discharged from the top part of the column 9 is fed to the solvent separation tank 12 via the line 11. Upon being fed to the tank 12, the mixture is separated into oily phase (azeotropic solvent) and water phase (collecting liquid). The water phase is fed to a reverse osmosis permeation step 15 via a circulating line 14. In this instant, it is possible to provide an additional step of collecting the azeotropic solvent residue dissolved in the water phase in a solvent collecting column by distillation. Alternatively, such an additional step may be omitted. Also, part or all of the discharge liquid (distillated water phase component) may be fed to the reverse osmosis permeation step. It is possible to mix part or all of the distillated water phase component with the discharge liquid and/or processed liquid that are or is discharged from an unillustrated ejector in the acrylic acid production process for feeding to the reverse osmosis permeation step.

According to the embodiment, the azeotropic solvent separated by the solvent separation means 12 is recycled to the azeotropic distillation column 9 via the line 13. It is needless to say that the arrangement is not limited to the one illustrated in FIG. 1. Such an azeotropic solvent separated by the solvent separation tank 12 may be fed to an unillustrated another step. Referring to the impermeated liquid and the permeated liquid separated in the reverse osmosis permeation step, the permeated liquid is recycled to the collecting column 2 via the line 3 as a collecting liquid. In this case, part or all of the collecting liquid may be recycled to the collecting column 2. In FIG. 1, the collecting liquid is recycled to the collecting column 2 via the circulating line 3. Alternatively, the collecting liquid may be recycled to any position of the acrylic acid production process. Further, a liquid including a collecting liquid other than the collecting liquid circulating in the line 3 may be replenished from a feeding source to the acrylic acid production apparatus via a line 17 connected to the appropriate position of the apparatus. As shown in FIG. 1, replenishing a liquid from the unillustrated feeding source via the line 17 is preferable because it is advantageous in securing a certain amount of collecting liquid required in the collecting column 3 and in further reducing the concentration of the byproducts remaining in the collecting liquid. It should be appreciated that the impermeated liquid is discharged outside of the apparatus via a line 16. In this instant, the impermeated liquid may be subjected to an arbitrary process or not subjected to such a process.

As mentioned above, according to this invention, polymerization of acrylic acid resulting from byproducts and precipitation of byproducts such as glyoxal can be securely prevented by bringing the discharged liquid from the (meth)acrylic acid production process such as mentioned above to a reverse osmosis permeation, thus securing long-term stable operation of the (meth)acrylic acid production apparatus.

Furthermore, the inventors of this application found that formaldehyde and glyoxal among a variety of byproducts contained in the discharged liquid, particularly, glyoxal, when condensed, may likely to accelerate polymerization of acrylic acid, and/or may likely to form reactants and precipitants caused by glyoxal. The inventors also found the following phenomenon. Glyoxal easily turns into dehydrates thereof in the presence of condensed water in the column, thus easily being condensed. Hydrates of glyoxal are condensed and heated in the column into oligomers. Such oligomers are likely to precipitate in the, column, resulting in blocking the column. The inventors found that the above precipitating phenomenon is unallowable if the concentration of glyoxal (including its hydrates) in the acrylic acid aqueous solution exceeds 0.1 mass %. In view of this, it is desirable to set the concentration of glyoxal (including its hydrates) in the (meth)acrylic aqueous solution at 0.1 mass % or lower, preferably at 0.05 mass % or lower, more preferably at 0.03 mass % or lower, and most preferably at 0.015 mass % or lower. In this embodiment, an (meth) acrylic acid aqueous solution is exemplified as a liquid containing (meth)acrylic acid.

Exemplified methods for obtaining above mentioned preferable liquid containing (meth)acrylic acid include lowering the concentration of impurities, such as ethylene, which are contained in the mixed gas including propylene, suppressing generation of glyoxal by controlling the oxidation reaction condition, modifying glyoxal by chemical treatment, and performing the aforementioned reverse osmosis permeation. Among these treatments, it is preferable to reduce at least the concentration of glyoxal (including its hydrates. Hereinafter, glyoxal including its hydrates are simply referred to as "glyoxal". The concentration of glyoxal is determined on the basis of molecular weight of glyoxal at 58.04.) in the permiated liquid. The reverse osmosis permeation is preferable because it does not affect the operating condition of the (meth)acrylic acid production apparatus or its influence is negligible, compared to the other conceivable methods. It is desirable to remove byproducts, preferably, glyoxal and formaldehyde, more preferably, glyoxal, formaldehyde, acetic acid, and formic acid while reducing the concentration thereof. The lower the concentration of byproducts in the permeable liquid is, the higher polymerization suppressing effect and precipitation suppressing effect in the azeotropic distillation column 9 be ensured. In view of this, it is desirable to set the removing ratio of glyoxal by a reverse osmosis membrane in the reverse osmosis permeation step at 30% or higher, preferably at 50% or higher, and more preferably at 70% or more, and furthermore preferably at 90% or higher. Further, to more securely preventing polymerization resulting from byproducts and precipitation of byproducts, it is desirable to remove glyoxal and formaldehyde as byproducts, preferably, glyoxal, formaldehyde, acetic acid, and formic acid as byproducts at 30% or more with respect to each byproduct, more preferably at 50% or more. The removing ratio in this specification is determined according to the following equation.

removing ratio (%)=(solute concentration of liquid fed to membrane−solute concentration of permeable liquid)/solute concentration of liquid fed to membrane×100

The kind of reverse osmosis membrane used in the reverse osmosis permeation step is not specifically limited. Exemplified components constituting the membrane are polyamide type such as cross-linked polyamides and aromatic polyamides; condensates of aliphatic amine type; heterocyclic polymer type; acetyl cellulose type; polyethylene type; polyvinyl alcohol type; and polyether type. Among these, it is desirable to use a reverse osmosis membrane having a high removing ratio with respect to glyoxal (to cope with high concentration of glyoxal in the impermeated liquid). Particularly, it is recommended to use a reverse osmosis membrane having a glyoxal removing ratio of 30% or more, preferably 50% or more, and furthermore preferably 70% or more. In view of this, it is desirable to use a reverse osmosis membrane including a high molecular membrane whose film layer is made of polyamide or polyvinyl alcohol.

The reverse osmosis membrane may include a variety of kinds of membranes such as asymmetric membranes and composite membranes. The module of such a reverse osmosis membrane is not specifically limited, and includes, e.g., a flat membrane module, a hollow fiber module, a spiral module, a cylindrical module, and a pleated module. Among these, a spiral module is desirable because it has a large membranous area, is easy in downsizing the apparatus, and is less likely to cause blocking of the column due to precipitants.

According to this embodiment, it is preferable to carry out the liquid separation by the reverse osmosis membrane in such a condition that pH of the liquid (distillated water phase component), which is to be processed by the reverse osmosis membrane, in the range from 2 to 10, and preferably, in the range from 2 to 7. Alternatively, it may be possible to subject the liquid to the reverse osmosis permeation after adding a pH adjuster to the collecting liquid.

The pressure of the liquid (distillated water phase component) to be fed to the reverse osmosis membrane differs depending on the total concentration of solute in the liquid. Generally, feeding the liquid at a smaller pressure may lessen the amount of the permeated liquid permeating through the membrane. In view of this, the area of the reverse osmosis membrane is required to be sufficiently large in order to permeate a certain amount of the liquid. Such an arrangement, however, makes the permeation unit using the reverse osmosis membrane large, which is not desirable in terms of installation. In view of this, it is recommended to set the liquid pressure at 0.3 MPa or higher, and preferably at 1 MPa or higher. On the other hand, feeding the liquid at an exceedingly large pressure may likely to break the membrane. In view of this, it is desirable to set the liquid pressure at 20 MPa or lower, preferably at 10 MPa or lower.

The temperature of the liquid (distillated water phase component) to be permeated through the reverse osmosis membrane is preferably 10° C. or higher, more preferably 20° C. or higher, and further more preferably 25° C. or higher, and preferably 50° C. or lower, more preferably 40° C. or lower, and furthermore preferably 35° C. or lower. When the liquid temperature exceeds 50° C., acrylic acid in the collecting liquid, permeated liquid, and/or impermeated liquid may polymerize, which is not desirable. When the liquid temperature is lowered than 10° C., it is likely that the amount of permeated liquid permeated through the membrane may be lessened, or precipitants generate in the collecting liquid, permeated liquid, and/or impermeated liquid, which is also not desirable. There is a case that the upper limit temperature of the liquid (distillated water phase component) may be determined depending on the allowable temperature of the liquid which is fed to the membrane (namely, maximal allowable temperature of the membrane is determined by the manufacturer of the membrane).

The amount of the liquid (distillated water phase component) to be fed to the reverse osmosis membrane is not specifically limited. In case of providing a processing step such as an azeotropic solvent separating step, the amount of the distillated water phase component is determined based on the amount of the liquid that has undergone the additional step. It is, however, desirable to feed 30% to 100% of the distillated water phase component, preferably 50% to 100%, more preferably 100% of the distillated water phase component from the azeotropic distillation column to the reverse osmosis membrane in order to prevent generation of polymerized acrylic acid and/or precipitation of byproducts.

The reverse osmosis permeation step includes a batch process and a continuous process. In the batch process, it is a general practice to permeate the permeated liquid while feeding all the amount of the impermeated liquid to the reverse osmosis membrane and to recycle the permeated liquid to the collecting step upon confirming that the permeated liquid reaches a predetermined amount (batch-wise). In the batch process, the impermeated liquid (condensed liquid) obtained batch-wise is discharged outside of the system. In the case where the amount of the impermeated liquid obtained batch-wise is smaller than the corresponding amount of the collecting liquid (distillated water phase component) to be fed to the reverse osmosis membrane, the solute concentration in the impermeated liquid is exceedingly raised, thereby raising the operative pressure of the membrane beyond the upper limit defined above, which is not desirable. In view of this, it is desirable to set the ratio of the amount of the impermeated liquid to the total amount of the liquid fed to the membrane at $\frac{1}{20}$ or higher, preferably at $\frac{1}{10}$ or higher. An exceedingly high ratio requires processing of a large amount of impermeated liquid as waste liquid, which is not desirable. Further, such an exceeding high ratio resultantly lowers the amount of permeated liquid permeating through the membrane. If the amount of the permeated liquid is lowered, it is necessary to replenish a large amount of collecting liquid (such as purified water for industrial use) from outside of the acrylic acid production apparatus, which is not economically desirable. In view of this, the ratio of the impermeated liquid to the total feeding liquid to the membrane is $\frac{1}{2}$ or lower, and preferably $\frac{1}{3}$ or lower.

In the continuous process, it is a general practice to introduce the liquid (distillated water phase component) to the reverse osmosis membrane, and to recycle part of the impermeated liquid to the membrane while discharging the remainder of the impermeated liquid (condensed liquid) outside of the permeation system (production process). Such an operation involves the following drawback. Specifically, in the case where the flow rate of the impermeated liquid to be discharged outside of the production apparatus is smaller than the amount of the liquid (distillated water phase component) to be fed to the membrane, the solute concentration of the impermeated liquid is exceedingly raised, and the operative pressure of the membrane exceeds the upper limit defined above, which is not desirable. In view of this, it is preferable to set the flow rate of the impermeated liquid to be discharged outside of the permeation unit to the total feeding liquid to the membrane at $\frac{1}{20}$ or more, preferably at $\frac{1}{10}$ or more. The flow rate of the impermeated liquid to be discharged outside of the permeation unit to the total feeding liquid is preferably $\frac{1}{2}$ or lower, more preferably $\frac{1}{3}$ or lower for the same reason as mentioned above in the case of batch process.

In the embodiment, particularly, in FIG. 1, liquid pressure/flow rate adjusting means such as a liquid feeding pump and a flow rate control valve are not illustrated. However, it is desirable to arrange pressure/flow rate adjusting means at such an appropriate position as to obtain the aforementioned pressures, etc. in conformance with the operation conditions of the apparatus in order to regulate the flow rate and pressure properly.

As mentioned above, according to the inventive method, polymerization of acrylic acid resulting from byproducts in the distillation step can be prevented, and generation of precipitants due to condensation of such byproducts can be effectively suppressed by removing the byproducts contained in the discharged liquid from the acrylic acid production apparatus (especially distillation unit as mentioned above) in a reverse osmosis permeation step and by reusing the processed liquid after the byproduct removal to the acrylic acid production process.

Hereinafter, the inventive method is described in details with reference to the examples. It should be appreciated that the inventive method is not restricted to the examples shown below.

EXAMPLE 1

The following experiment was conducted according to the acrylic acid production process as illustrated in FIG. 1. Propylene and molecular oxygen-containing gas were fed to an unillustrated catalytic gas-phase reactor (provided with an intermediate tube plate partitioning the reactor into upper and lower chambers) to obtain acrylic acid containing gas by catalytic gas-phase oxidation. Thus obtained acrylic acid containing gas was fed to the collecting column 2 via the line 1 to contact with a collecting liquid fed into the collecting column 2 via the line 3, thereby collecting crude acrylic acid contained in the gas, in an aqueous solution. The acrylic acid aqueous solution obtained in this experiment contained byproducts such as acrolein, formaldehyde, furfural, glyoxal, acetic acid, and formic acid. The acrylic acid aqueous solution was fed to the stripping column 6 via the line 4 for stripping the acrolein contained in the aqueous solution. Thus, the acrylic acid aqueous solution containing 30 mass % of water, 3.0 mass % of acetic acid, and 0.009 mass % of glyoxal was obtained. Then, the aqueous solution was fed to the azeotropic distillation column 9 via the line 7. The residue gas discharged from the collecting column 2 and the acrolein discharged from the stripping column 6 were respectively fed to the catalytic gas-phase reactor via the line 5 and the line 8. The azeotropic distillation column 9 having an inner diameter of 105 mm was provided with fifty stainless sieve trays vertically spaced apart at an interval of 147 mm. The column 9 was further provided with a distillation tube and a reflux liquid feeding tube at a top part thereof, a mixed gas liquid feeding tube and a polymerization inhibitor feeding tube at an intermediate part thereof (around the twentieth tray from the top), and a bottom liquid drawing tube and an oxygen feeding tube at a bottom part thereof. The distillation of the acrylic acid aqueous solution in the column 9 was carried out with use of toluene as an azeotropic solvent. The polymerization inhibitor was used in the amount of 10 ppm of copper dibutyldithiocarbamate, 100 ppm of phenothiazine, 100 ppm of hydroquinone, 10 ppm of manganese acetate to the evaporated vapor amount of acrylic acid. Copper dibutyldithiocarbamate and phenothiazine were fed to the column 9 through the top part thereof in a state that these compounds were dissolved in the reflux liquid. The other polymerization inhibitors were fed to the column 9 through the intermediate part thereof in a state that these compounds were dissolved in the acrylic acid aqueous solution. Further, 0.3 volumetric % of molecular oxygen to the evaporated vapor amount of acrylic acid was fed from the bottom part of the column 9. It should be noted that the evaporated vapor amount of acrylic acid is equivalent to the quantity of heat transferred from an unillustrated reboiler of the azeotropic distillation column 9 to the column, and corresponds to the total amount of vapors of monomers vaporized from the bottom liquid.

The operating condition of the acrylic acid production apparatus for steadily performing the above process was as follows. The temperature at the top part of the azeotropic distillation column 9 was 50° C. the temperature at the bottom part of the column 9 was 105° C., the pressure at the column top was 170 hPa, the reflux ratio (total number of moles of reflux liquid per unit time/total number of moles of distillate per unit time) was 1.43, and the feeding rate of the acrylic acid aqueous solution was 8.5 litter/hour. The distillate discharged from the top part of the column 9 was fed to the tank 12 for separation into the azeotropic solvent (oily phase) and the collecting liquid (water phase). The collecting liquid contained 7.5 mass % of acetic acid, 1.8 mass % of acrylic acid, 1.7 mass % of formaldehyde, 0.6 mass % of formic acid, 0.02 mass % of acrolein, and 0.03 mass % of glyoxal. The drawing liquid discharged from the column bottom contained 97.5 mass % of acrylic acid, 0.03 mass % of acetic acid, 0.02 mass % of water, and 2.45 mass % of other ingredients. Toluene contained in the drawing liquid was below the detectable limit (1 ppm). The collecting liquid (water phase) which passed the tank 12 was temporarily stored in an unillustrated tank via the line 14. Thereafter, the collecting liquid was fed to the reverse osmosis permeation unit 15 batch-wise, thereby obtaining a permeated liquid in the amount corresponding to 4/5 of the fed collecting liquid (water phase) and an impermeated liquid in the amount corresponding to 1/5 of the fed collecting liquid (water phase). The reverse osmosis membrane used in the permeation unit 15 was a membrane NTR-759HR manufactured by Nitto Denko Kabushiki Kaisha. The total amount of the permeated liquid was recycled to the collecting column 2 as absorbent water (collecting liquid) for absorbing the acrylic-acid-containing gas. The impermeated liquid was discharged out of the system via the line 16. The permeated liquid contained 4.3 mass % of acetic acid, 0.9 mass % of acrylic acid, 1.0 mass % of formaldehyde, 0.3 mass % of formic acid, 0.01 mass % of acrolein, and 0.001 mass % of glyoxal. Purified water for industrial use in the amount corresponding to the discharged amount of the impermeated liquid was replenished to the recycling permeated liquid via the line 17 to feed the permeated liquid along with the purified water to the collecting column 2 via the line 3. Acrylic acid production was carried out according to the aforementioned process and under the above conditions for thirty consecutive days. As a result of the experiment, it was verified that the azeotropic distillation column 9 was operated stably for the period. After the predetermined period was over, the operation of the column 9 was suspended, and the interior of the column 9 was checked to find whether byproducts precipitated. As a result of checking, no precipitant of byproducts and no polymerized acrylic acid were found.

COMPARATIVE EXAMPLE 1

Azeotropic distillation of an acrylic acid aqueous solution was carried out in the similar manner as Example 1 except the following. Specifically, after feeding the distillate discharged from the column 9 to the tank 12 for separation into the azeotropic solvent (oily phase) and the collecting liquid (water phase), 4/5 of the collecting liquid after passing the tank 12 was recycled to the collecting column 2 without being subjected to a reverse osmosis permeation, and 1/5 of the collecting liquid was discharged out of the apparatus as waste water. Then, purified water for industrial use in the amount corresponding to the discharged water was replenished to the collecting liquid for recycling to the collecting column 2. Thus obtained acrylic acid aqueous solution contained 30 mass % of water, 3.0 mass % of acetic acid, and 0.04 mass % of glyoxal. The column 9 was brought to a continuous operation in the above conditions. At an initial stage of the operation, acrylic acid as a product having the same purity as in Example 1 was produced. However, at the $25^{th}$ day from the start of the operation, polymerized acrylic acid was found in the drawing liquid discharged from the column bottom. At the $27^{th}$ day, the operation was suspended, and the column 9 was disassembled for checking. As a result of checking, polymerized acrylic acid and precipitants of byproducts were found in the column 9.

COMPARATIVE EXAMPLE 2

Azeotropic distillation of an acrylic acid aqueous solution was carried out in the similar manner as Comparative Example 1 (no reverse osmosis membrane was used) except that 19/20 of the collecting liquid (water phase) was recycled to the collecting column 2, and 1/20 of the collecting liquid was discharged out of the apparatus as waste water, and purified water for industrial use in the amount corresponding to the waste water was replenished to the collecting liquid for recycling. The acrylic acid aqueous solution obtained in this experiment contained 30 mass % of water, 3.0 mass % of acetic acid, and 0.07 mass % of glyoxal. The column 9 was brought to a continuous operation in the above conditions. At the initial stage of the operation, the operation in the similar manner as Example 1 was executable. However, around the $12^{th}$ day from the start of the operation, polymerized acrylic acid was started to generate in the bottom liquid. At the $14^{th}$ day, the operation of the column 9 was suspended, and the column 9 was disassembled for checking. As a result of checking, polymerized acrylic acid and precipitants of byproducts were found.

COMPARATIVE EXAMPLE 3

Azeotropic distillation of an acrylic acid aqueous solution was carried out in the similar manner as Comparative Example 1 (no reverse osmosis membrane was used) except that $99/100$ of the collecting liquid (water phase) was recycled to the collecting column 2, and $1/100$ of the collecting liquid was discharged out of the apparatus as waste water, and purified water for industrial use in the amount corresponding to the waste water was replenished to the collecting liquid for recycling. The acrylic acid aqueous solution obtained in this experiment contained 30 mass % of water, 3.0 mass % of acetic acid, and 0.12 mass % of glyoxal. The column 9 was brought to a continuous operation in the above conditions. At the initial stage of the operation, the operation in the similar manner as Example 1 was executable. However, around the $7^{th}$ day from the start of the operation, pressure loss occurred in the column 9, thereby failing to perform stable operation. Thus, the operation of the column 9 was immediately suspended, and the column 9 was disassembled for checking. As a result of checking, polymerized acrylic acid and a bulky amount of precipitants of byproducts were found.

EXAMPLE 2

Azeotropic distillation of an acrylic acid aqueous solution was carried out in the similar manner as Example 1 except that the operating condition was controlled so that the permeated liquid in the amount corresponding to ½ of the collecting liquid (water phase) fed to the permeation unit 15 was obtained and that the impermeated liquid in the amount corresponding to ½ of the fed collecting liquid (water phase) was obtained. The acrylic acid aqueous solution obtained in this experiment contained 30 mass % of water, 3.0 mass % of acetic acid, and 0.009 mass % of glyoxal. The permeated liquid contained 3.8 mass % of acetic acid, 0.8 mass % of acrylic acid, 0.9 mass % of formaldehyde, 0.3 mass % of formic acid, 0.01 mass % of acrolein, and 0.001 mass % of glyoxal. Purified water for industrial use corresponding to the amount of the discharged impermeated liquid was replenished to the permeated liquid for recycling to the collecting column 2 via the line 17. The column 9 was brought to a continuous operation in the above conditions for thirty consecutive days. As a result of the experiment, acrylic acid in a constant concentration was obtained, and the operation condition of the column 9 was also stable. Furthermore, as a result of checking the interior of the column 9 after suspending the operation thereof, no polymerized acrylic acid and no precipitants of byproducts were found. The collecting liquid (water phase) discharged from the top part of the column 9 contained 7.1 mass % of acetic acid, 1.7 mass % of acrylic acid, 1.7 mass % of formaldehyde, 0.5 mass % of formic acid, 0.02 mass % of acrolein, and 0.03 mass % of glyoxal.

EXAMPLE 3

Azeotropic distillation of an acrylic acid aqueous solution was carried out in the similar manner as Example 1 except that a membrane NTR-729HF manufactured by Nitto Denko Kabushiki Kaisha was used as a reverse osmosis membrane and that the operating condition was controlled so that the permeated liquid in the amount corresponding to ⅘ of the collecting liquid (water phase) fed to the permeation unit 15 was obtained and that the impermeated liquid in the amount corresponding to ⅕ of the fed collecting liquid was obtained. The acrylic acid aqueous solution obtained in this experiment contained 30 mass % of water, 3.0 mass % of acetic acid, and 0.016 mass % of glyoxal. The permeated liquid contained 7.1 mass % of acetic acid, 1.7 mass % of acrylic acid, 1.6 mass % of formaldehyde, 0.5 mass % of formic acid, 0.01 mass % of acrolein, and 0.02 mass % of glyoxal. Purified water for industrial use corresponding to the amount of the discharged impermeated liquid was replenished to the permeated liquid for recycling to the collecting column 2 via the line 17. The column 9 was brought to a continuous operation in the above conditions for thirty consecutive days. As a result of the experiment, acrylic acid in a constant concentration was obtained from the bottom of the column 9, and the operation condition of the column 9 was also stable. Furthermore, as a result of checking the interior of the column 9 after suspending the operation thereof upon lapse of the period, no polymerized acrylic acid was found but a negligible amount of precipitants of byproducts was found. The collecting liquid (water phase) discharged from the top part of the column 9 contained 8.2 mass % of acetic acid, 2.2 mass % of acrylic acid, 1.8 mass % of formaldehyde, 0.6 mass % of formic acid, 0.02 mass % of acrolein, and 0.045 mass % of glyoxal.

EXAMPLE 4

Azeotropic distillation of an acrylic acid aqueous solution was carried out in the similar manner as Example 3 except that the operating condition was controlled so that the permeated liquid in the amount corresponding to ½ of the collecting liquid (water phase) fed to the permeation unit 15 was obtained and that the impermeated liquid in the amount corresponding to ½ of the fed collecting liquid was obtained. The acrylic acid aqueous solution obtained in this experiment contained 30 mass % of water, 3.0 mass % of acetic acid, and 0.012 mass % of glyoxal. The permeated liquid contained 6.9 mass % of acetic acid, 1.6 mass % of acrylic acid, 1.4 mass % of formaldehyde, 0.4 mass % of formic acid, 0.01 mass % of acrolein, and 0.01 mass % of glyoxal. Purified water for industrial use corresponding to the amount of the discharged impermeated liquid was replenished to the permeated liquid for recycling to the collecting column 2 via the line 17. The column 9 was brought to a continuous operation in the above conditions for thirty consecutive days. As a result of the experiment, acrylic acid in a constant concentration was obtained, and the operation condition of the column 9 was also stable. Furthermore, as a result of checking the interior of the column 9 after suspending the operation thereof upon lapse of the period, no polymerized acrylic acid and precipitants of byproducts were found. The collecting liquid (water phase) discharged from the top part of the column 9 contained 7.9 mass % of acetic acid, 2.1 mass % of acrylic acid, 1.8 mass % of formaldehyde, 0.6 mass % of formic acid, 0.02 mass % of acrolein, and 0.035 mass % of glyoxal.

This invention is constructed as mentioned above. According to the inventive method, subjecting the discharged liquid from the (meth)acrylic acid production process to a reverse osmosis permeation to obtain a permeated liquid and recycling the permeated liquid as a collecting liquid enables to effectively reduce the concentration of byproducts in the acrylic acid aqueous solution. In this arrangement, polymerization of acrylic acid resulting from byproducts and precipitation of such byproducts can be securely prevented. With this arrangement, the (meth)acrylic acid production process can be carried out stably for a long term.

This application is based on Japanese patent application serial No. 2001-304050 filed on Sep. 28, 2001, whose priority is claimed under Paris convention, thus the contents thereof is incorporated by reference.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A method for producing (meth)acrylic acid comprising the steps of obtaining a mixed gas containing (meth)acrylic acid and glyoxal by catalytic gas phase oxidation using propylene and/or acrolein, or using at least one compound selected from the group consisting of isobutylene, t-butyl alcohol, and methacrolein, contacting the mixed gas with a collecting liquid to obtain a (meth)acrylic acid aqueous solution, separating the (meth)acrylic acid aqueous solution into (meth)acrylic acid and a discharged liquid containing glyoxal by distillation, separating a part or all of the discharged liquid into a permeated liquid and an impermeated liquid containing glyoxal with the use of reverse osmosis membrane, thereby reducing a concentration of glyoxal contained in the permeated liquid, and recycling a part or all of the permeated liquid by circulation as the collecting liquid.

2. The method for producing (meth)acrylic acid according to claim 1, further comprising lowering a concentration of glyoxal in the (meth)acrylic acid aqueous solution to 0.1 mass % or less by recycling the permeated liquid from which the glyoxal is reduced.

3. The method for producing (meth)acrylic acid according to claim 1, further comprising lowering a concentration of glyoxal in the (meth)acrylic acid aqueous solution to 0.03 mass % or less by recycling the permeated liquid from which the glyoxal is reduced.

4. The method for producing (meth)acrylic acid according to claim 1, further comprising lowering a concentration of glyoxal in the (meth)acrylic acid aqueous solution to 0.015 mass % or less by recycling the permeated liquid from which the glyoxal is reduced.

5. The method for producing (meth)acrylic acid according to claim 1, wherein the (meth)acrylic acid aqueous solution is separated into (meth)acrylic acid and the discharged liquid containing glyoxal by azeotropic distillation with an azeotropic solvent.

6. The method for produding (meth)acrylic acid according to claim 1, further comprising reducing a content of acrolein remaining in the (meth)acrylic acid solution prior to distillation.

* * * * *